United States Patent [19]

Müller-Gliemann et al.

[11] Patent Number: 5,527,809
[45] Date of Patent: Jun. 18, 1996

[54] SUBSTITUTED IMIDAZO[4,5-B]PYRIDINES AND BENZIMIDAZOLES

[75] Inventors: Matthias Müller-Gliemann, Solingen; Jürgen Dressel, Radevormwald; Peter Fey, Wuppertal; Rudolf H. Hanko, Düsseldorf; Walter Hübsch, Wuppertal; Thomas Krämer, Wuppertal; Ulrich E. Müller, Wuppertal; Martin Beuck, Erkrath; Stanislav Kazda, Wuppertal; Stefan Wohlfeil, Hilden; Andreas Knorr, Erkrath; Johannes-Peter Stasch, Solingen; Siegfried Zaiss, Wuppertal, all of Germany

[73] Assignee: Bayer Aktiengesellschaft, Leverkusen, Germany

[21] Appl. No.: 187,925

[22] Filed: Jan. 27, 1994

[30] Foreign Application Priority Data

Feb. 3, 1993 [DE] Germany .......................... 43 02 956.6

[51] Int. Cl.⁶ ...................... A61K 31/435; C07D 471/04
[52] U.S. Cl. ............................................. 514/303; 546/118
[58] Field of Search ............................. 546/118; 514/303

[56] References Cited

U.S. PATENT DOCUMENTS

| 5,128,355 | 7/1992 | Carini et al. | 514/381 |
| 5,138,069 | 8/1992 | Carini et al. | 548/253 |
| 5,153,197 | 10/1992 | Carini et al. | 514/255 |
| 5,155,118 | 10/1992 | Carini et al. | 514/381 |
| 5,240,938 | 8/1993 | Greenlee | 514/303 |

FOREIGN PATENT DOCUMENTS

| 0513533 | 11/1992 | European Pat. Off. . |
| 0513533A2 | 11/1992 | European Pat. Off. . |
| 4200954A1 | 10/1992 | Germany . |
| 91/11999 | 8/1991 | WIPO . |

OTHER PUBLICATIONS

Chemical Abstracts 118:191734 of DE 4200954 published 29 Oct. 1992, 1992.
Chemical Abstracts 118:234063 of EP 513533 published 19 Nov. 1992, 1992.
The Journal of Cell Biology, vol. 50, 1971, pp. 172–186; "The Smooth Muscle Cell", R. Ross.

*Primary Examiner*—C. Warren Ivy
*Assistant Examiner*—D. Margaret M. Mach
*Attorney, Agent, or Firm*—William C. Gerstenzang; Sprung Horn Kramer & Woods

[57] ABSTRACT

Substituted imidazo[4,5-b]pyridines and benzimidazoles are prepared by reacting imidazo[4,5-b]pyridines or benzimidazoles with appropriately substituted benzyl halides. The substituted imidazo[4,5-b]pyridines or benzimidazoles can be employed as active compounds in medicaments, in particular for the treatment of arterial hypertension and atherosclerosis.

7 Claims, No Drawings

SUBSTITUTED IMIDAZO[4,5-B]PYRIDINES AND BENZIMIDAZOLES

The invention relates to substituted imidazo[4,5-b]-pyridines and benzimidazoles, processes for their preparation and their use in medicaments, in particular as hypotensive and antiatherosclerotic agents.

It is known that renin, a proteolytic enzyme, eliminates the decapeptide angiotensin I from angiotensinogen in vivo, and the angiotensin I is in turn degraded in the lung, the kidneys or other tissues to give the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, cardiac muscle cells and smooth muscle cells, these growing and proliferating in an increased manner in various disease states (for example hypertension, atherosclerosis and cardiac insufficiency).

Apart from inhibition of renin activity, a possible starting point for intervention in the renin-angiotensin system (RAS) is the inhibition of the activity of angiotension-converting enzyme (ACE) and the blockade of angiotensin II receptors.

The present invention relates to substituted imidazo[4,5-b]pyridines and benzimidazoles of the general formula (I)

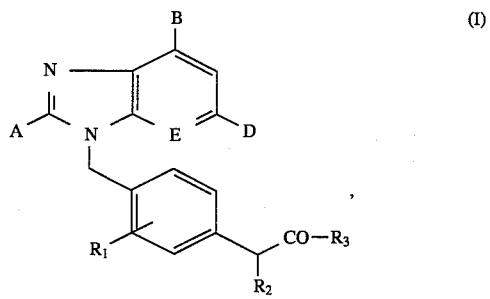

in which

A represents straight-chain or branched alkyl or alkenyl in each case having up to 8 carbon atoms, or represents cycloalkyl having 3 to 8 carbon atoms, or represents phenyl which is optionally substituted by halogen, nitro, hydroxyl, trifluoromethyl, trifluoromethoxy, straight-chain or branched alkyl, alkoxy or alkoxycarbonyl in each case having up to 6 carbon atoms, cyano or carboxyl, B and D are identical or different and represent hydrogen, halogen or straight-chain or branched alkyl having up to 8 carbon atoms, E represents a nitrogen atom or the —CH— group, $R^1$ represents hydrogen, halogen, nitro, hydroxyl, trifluoromethyl, trifluoromethoxy, straight-chain or branched alkyl, alkoxy or alkoxycarbonyl in each case having up to 6 carbon atoms, cyano or carboxyl, $R^2$ represents hydrogen, cycloalkyl having 3 to 8 carbon atoms or straight-chain or branched alkyl having up to 8 carbon atoms, which is optionally substituted by phenyl, carboxyl, hydroxyl, halogen, cyano, cycloalkyl having 3 to 8 carbon atoms or by straight-chain or branched alkoxy or alkoxycarbonyl in each case having up to 6 carbon atoms, $R^3$ represents hydroxyl or straight-chain or branched alkoxy having up to 8 carbon atoms, or represents a group of the formula

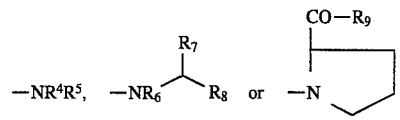

in which $R^4$, $R^5$ and $R^6$ are identical or different and denote hydrogen, straight-chain or branched alkyl having up to 6 carbon atoms or phenyl, or $R^4$ has the abovementioned meaning and $R^5$ denotes a group of the formula $-SO_2-R^{10}$, in which $R^{10}$ denotes straight-chain or branched alkyl having up to 6 carbon atoms, which is optionally substituted by phenyl, or denotes phenyl which is optionally substituted by straight-chain or branched alkyl having up to 4 carbon atoms, $R^7$ denotes phenyl which is optionally substituted up to 2 times by identical or different substituents from the series consisting of halogen, nitro, hydroxyl, trifluoromethyl, trifluoromethoxy, straight-chain or branched alkyl, alkoxy or alkoxycarbonyl in each case having up to 6 carbon atoms, cyano, carboxyl, cycloalkyl having 3 to 8 carbon atoms and phenyl, $R^8$ denotes carboxyl or straight-chain or branched alkoxycarbonyl having up to 6 carbon atoms, or denotes a group of the formula $-CH_2-OR^{11}$, $-CO-NR^{12}R^{13}$ or $-CH_2NR^{12}R^{13}$, in which $R^{11}$ denotes hydrogen, phenyl or straight-chain or branched alkyl having up to 6 carbon atoms and $R^{12}$ and $R^{13}$ have the abovementioned meaning of $R^4$ and $R^5$ and are identical to or different from this, $R^9$ denotes hydroxyl, benzyloxy or straight-chain or branched alkoxy having up to 8 carbon atoms, or denotes a group of the formula

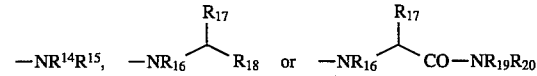

in which $R^{14}$ and $R^{15}$ have the abovementioned meaning of $R^4$ and $R^5$ and are identical to or different from this, $R^{16}$ has the abovementioned meaning of $R^6$ and is identical to or different from this, $R^{17}$ and $R^{18}$ in each case have the abovementioned meaning of $R^7$ and $R^8$ and are identical to or different from this and $R^{19}$ and $R^{20}$ have the abovementioned meaning of $R^4$ and $R^5$ and are identical to or different from this, if appropriate in an isomeric form, and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the substituted imidazo[4,5-b]pyridines and benzimidazoles can be salts of the substances according to the invention with mineral acids, carboxylic acids or sulphonic acids. Particularly preferred salts, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or from organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which either behave as image and mirror image (enantiomers), or which do not behave as image and mirror image (diastereomers). The invention relates both to the enantiomers or diastereomers or to their respective mixtures. Like the diastereomers, the racemic forms can be separated into the stereoisomerically uniform constituents in a known manner.

Preferred compounds of the general formula (I) are those in which

A represents straight-chain or branched alkyl or alkenyl in each case having up to 6 carbon atoms, or represents cyclopropyl, cyclobutyl, cyclopentyl, cyclohexyl or cycloheptyl or represents phenyl which is optionally substituted by fluorine, chlorine, bromine, trifluoromethyl, carboxyl or straight-chain or branched alkyl, alkoxy or alkoxycarbonyl in each case having up to 4 carbon atoms, B and D are identical or different and represent hydrogen or straight-chain or branched alkyl having up to 6 carbon atoms, E represents a nitrogen atom or the —CH— group, $R^1$ represents hydrogen, fluorine, chlorine, bromine, trifluoromethyl, carboxyl or straight-chain or branched alkyl, alkoxy or alkoxycarbonyl in each case having up to 4 carbon atoms, $R^2$ represents hydrogen, cyclopropyl, cyclopentyl, cyclohexyl or cycloheptyl or represents straight-chain or branched alkyl having up to 6 carbon atoms, which is optionally substituted by phenyl, fluorine, chlorine, bromine, cyclopentyl, cyclohexyl or by straight-chain or branched alkoxy or alkoxycarbonyl in each case having up to 4 carbon atoms, $R^3$ represents hydroxyl or straight-chain or branched alkoxy having up to 6 carbon atoms, or represents a group of the formula

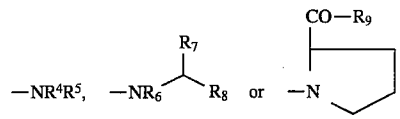

in which $R^4$ and $R^5$ and $R^6$ are identical or different and denote hydrogen or straight-chain or branched alkyl having up to 4 carbon atoms, or $R^4$ has the abovementioned meaning and $R^5$ denotes a group of the formula —$SO_2$—$R^{10}$, in which $R^{10}$ denotes straight-chain or branched alkyl having up to 4 carbon atoms, which is optionally substituted by phenyl, or denotes phenyl which is optionally substituted by straight-chain or branched alkyl having up to 3 carbon atoms, $R^7$ denotes phenyl which is optionally substituted up to 2 times by identical or different substituents from the series consisting of fluorine, chlorine, bromine, trifluoromethyl, carboxyl, straight-chain or branched alkyl, alkoxy or alkoxycarbonyl in each case having up to 4 carbon atoms, cyclopentyl, cyclohexyl or phenyl, denotes carboxyl or straight-chain or branched alkoxycarbonyl having up to 4 carbon atoms, or denotes a group of the formula —$CH_2$—$OR^{11}$, —CO—$NR^{12}R^{13}$ or —$CH_2NR^{12}R^{13}$, in which $R^{11}$ denotes hydrogen or phenyl, or straight-chain or branched alkyl having up to 4 carbon atoms and $R^{10}$ and $R^{13}$ have the abovementioned meaning of $R^4$ and $R^5$ and are identical to or different from these, $R^9$ denotes hydroxyl, benzyloxy or straight-chain or branched alkoxy having up to 6 carbon atoms, or denotes a group of the formula

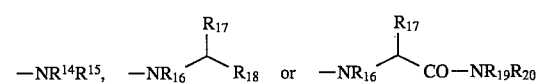

in which $R^{14}$ and $R^{15}$ have the abovementioned meaning of $R^4$ and $R^5$ and are identical to or different from this, $R^{16}$ has the abovementioned meaning of $R^6$ and is identical to or different from this, $R^{17}$ and $R^{18}$ in each case have the abovementioned meaning of $R^7$ and $R^8$ and are identical to or different from this and $R^{19}$ and $R^{20}$ have the abovementioned meaning of $R^4$ and $R^5$ and are identical to or different from this, if appropriate in an isomeric form, and their salts.

Particularly preferred compounds of the general formula (I) are those
in which

A represents straight-chain or branched alkyl or alkenyl in each case having up to 4 carbon atoms, or represents cyclopropyl, cyclopentyl, cyclohexyl or cycloheptyl, or represents phenyl, B and D are identical or different and represent hydrogen, methyl or ethyl, E represents a nitrogen atom or the —CH— group, $R^1$ represents hydrogen, fluorine, chlorine, bromine, trifluoromethyl, trifluoromethoxy or methyl, $R^2$ represents hydrogen, cyclopropyl, cyclopentyl, cyclohexyl, cycloheptyl, benzyl or straight-chain or branched alkyl, which is optionally substituted by cyclopentyl or cyclohexyl, $R^3$ represents hydroxyl or straight-chain or branched alkoxy having up to 4 carbon atoms, or represents a group of the formula

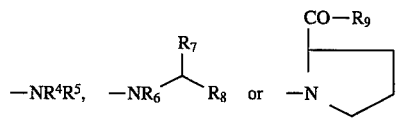

in which $R^4$, $R^5$ and $R^6$ are identical or different and denote hydrogen or methyl
or
$R^4$ has the abovementioned meaning
and
$R^5$ denotes a group of the formula $-SO_2-R^{10}$,
in which
$R^{10}$ denotes methyl, benzyl or p-tolyl,
$R^7$ denotes phenyl which is optionally substituted by fluorine, chlorine, bromine, trifluoromethyl, trifluoromethoxy or methyl,
$R^8$ denotes carboxyl or straight-chain or branched alkoxycarbonyl having up to 3 carbon atoms, or denotes a group of the formula $-CH_2O-R^{11}$, $-CO-NR^{12}R^{13}$ or $-CH_2NR^{12}R^{13}$
in which
$R^{11}$ denotes hydrogen or straight-chain or branched alkyl having up to 3 carbon atoms
and
$R^{12}$ and $R^{13}$ have the abovementioned meaning of $R^4$ and $R^5$ and are identical to or different from this,
$R^9$ denotes hydroxyl, benzyloxy or straight-chain or branched alkoxycarbonyl having up to 4 carbon atoms, or
denotes a group of the formula

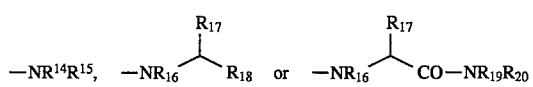

in which
$R^{14}$ and $R^{15}$ have the abovementioned meaning of $R^4$ and $R^5$ and are identical to or different from this,
$R^{16}$ has the abovementioned meaning of $R^6$ and is identical to or different from this,
$R^{17}$ and $R^{18}$ in each case have the abovementioned meaning of $R^7$ and $R^8$ and are identical to or different from this
and
$R^{19}$ and $R^{20}$ have the abovementioned meaning of $R^4$ and $R^5$ and are identical to or different from this,
if appropriate in an isomeric form, and their salts.
Very particularly preferred compounds of the formula (I) are those in which
A represents straight-chain or branched alkyl having up to 4 carbon atoms, or represents cyclopropyl or cyclopentyl, or represents phenyl,
B and D are identical or different and represent hydrogen or methyl,
E represents a nitrogen atom or the CH group,
$R^1$ represents hydrogen, fluorine or chlorine,
$R^2$ represents hydrogen, cyclopentyl, cyclohexyl or cycloheptyl, or represents straight-chain or branched alkyl having up to 4 carbon atoms,
and $R^3$ represents hydroxyl, straight-chain or branched alkoxy having up to 4 carbon atoms or represents a group of the formula

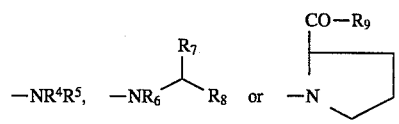

in which
$R^4$ and $R^6$ are identical or different and denote hydrogen or methyl,
$R^5$ denotes a group of the formula $-SO_2R^{10}$,
in which
$R^{10}$ denotes methyl or p-tolyl,
$R^7$ denotes phenyl which can optionally be substituted by fluorine, chlorine or methyl,
$R^8$ denotes the group $-CH_2-OH$ or $CO-NH_2$,
$R^9$ denotes hydroxyl, straight-chain or branched alkoxycarbonyl having up to 4 carbon atoms, or a group of the formula

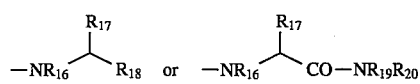

in which
$R^{14}$, $R^{15}$, and $R^{20}$ have the abovementioned meaning of $R^4$ and $R^5$ and are identical to or different from this,
$R^{16}$ has the abovementioned meaning of $R^6$ and is identical to or different from this,
$R^{17}$ and $R^{18}$ in each case have the abovementioned meaning of $R^{17}$ and $R^8$ and are identical to or different from this,
if appropriate in an isomeric form, and their salts.
In addition, a process for the preparation of the compounds of the general formula (I) according to the invention has been found, characterized in that
compounds of the general formula (II)

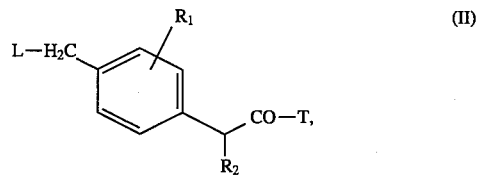

in which
$R^1$ and $R^2$ have the abovementioned meaning,
L represents a typical leaving group such as, for example, chlorine, bromine, iodine, tosylate or mesylate, preferably bromine,
and
T represents straight-chain or branched $(C_1-C_4)$-alkoxy,
are first reacted with compounds of the general formula (III)

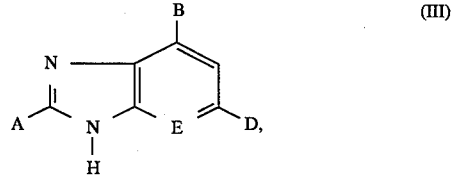

in which
A, B, D and E have the abovementioned meaning, in inert solvents, if appropriate in the presence of a base and if appropriate under a protective gas atmosphere, to give compounds of the general formula (IV)

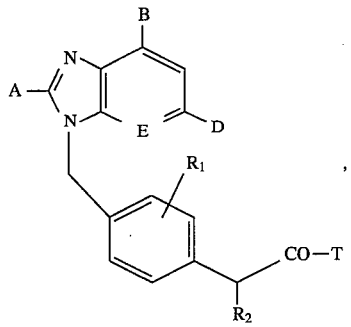

(IV)

in which

A, B, D, E, T, $R^1$ and $R^2$ have the abovementioned meaning, and in the case of the acids ($R^3$=OH) the esters are hydrolyzed, and in the case of the amides and sulphonamides, starting from the acids, if appropriate with prior activation, are reacted in inert solvents, if appropriate in the presence of a base and/or dehydrating agent, with amines and phenyl glycinols of the general formulae (V), (VI) and (VII) $HNR^4R^5$ (V), $HNR^6$—$CHR^7R^8$ (VI) or

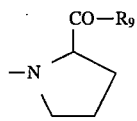

(VII)

in which $R^4$, $R^5$, $R^6$, $R^7$, $R^8$ and $R^9$ have the abovementioned meaning, and, if appropriate, the substituents A, B, D and $R^1$ are varied according to customary methods, and, if appropriate, the isomers are separated, and in the case of the preparation of the salts are reacted with an appropriate base or acid, and in the case of the esters, starting from the activated carboxylic acids, are reacted with the appropriate alkoxides.

The process according to the invention can be illustrated by way of example by the following reaction scheme:

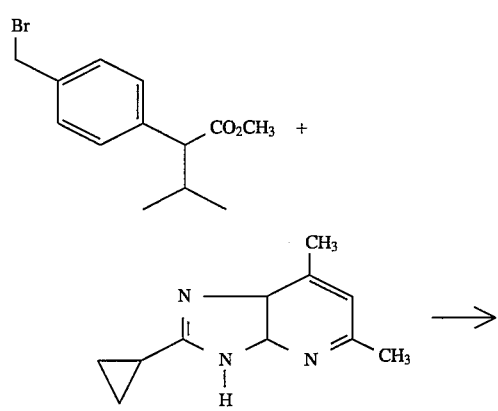

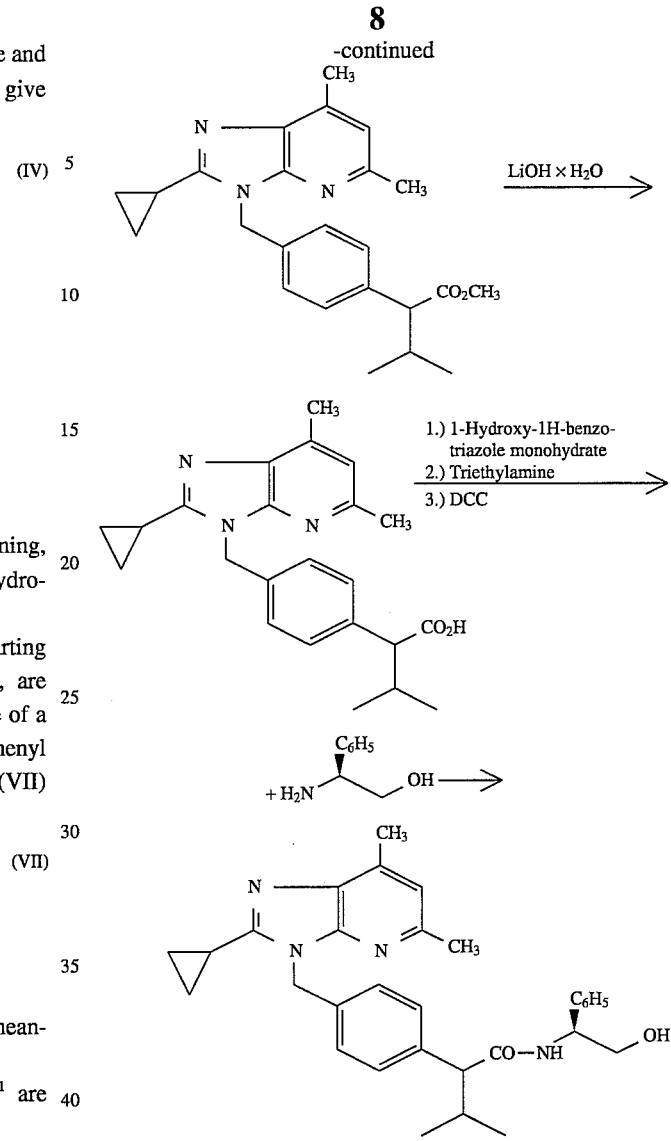

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane, or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoroustriamide acetonitrile, acetone or nitromethane. It is also possible to use mixtures of the solvents mentioned. Dimethylformamide and tetrahydrofuran are preferred.

The bases employed for the process according to the invention can in general be inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate or caesium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl($C_1$–$C_6$)amines) such as triethylamine, or heterocycles such as 1,4-diazabicyclo-[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium or their hydrides such as sodium hydride as bases. Sodium hydride, potassium carbonate, triethylamine, pyridine and potassium tert-butoxide are preferred.

In general the base is employed in an amount from 0.05 mol to 10 mol, preferably from 1 mol to 2 mol, relative to 1 mol of the compound of the formula (III).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is preferably carried out using acids such as, for example, trifluoroacetic acid, acetic acid, hydrochloric acid, hydrochloric acid/dioxane, hydrobromic acid, methanesulphonic acid, sulphuric acid or perchloric acid, particularly preferably using trifluoroacetic acid or hydrochloric acid/dioxane.

The hydrolysis is in general carried out in a temperature range from 0° C. to +100° C. preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has also proven advantageous in this case in the preparation of the carboxylic acids to acidify the basic reaction mixture from the hydrolysis in a second step without isolation of the carboxylates. The acids can then be isolated in a customary manner.

The amidation and the sulphoamidation are in general carried out in one of the abovementioned solvents, preferably in tetrahydrofuran or dichloromethane.

The amidation or sulphoamidation can proceed starting from the compounds of the general formula (IV), if appropriate via the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

The amidation or sulphoamidation is in general carried out in a temperature range from −50° C. to +80° C., preferably from −30° C. to +20° C., and at normal pressure.

In addition to the abovementioned bases, suitable bases for this reaction are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formula (V), (VI) or (VII).

Acid-binding agents which can be employed for the amidation or sulphoamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[4.3.0] non-5-ene (DBN) or 1,8-diazabicyclo[5.4.0] undec-7-ene (DBU). Triethylamine is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate, or benzotriazolyloxy-tris-(dimethylamino)phosphonium hexafluorophosphate or diphenylphosphoryl azide or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The compounds of the general formula (II) are known in some cases or are new and can then be prepared, for example, by reacting the corresponding 4-methyl compounds in the sense of a substitution, for example by halogenation in the presence of one of the abovementioned bases and/or auxiliaries and one of the solvents.

The compounds of the general formulae (III), (V), (VI) and (VII) are in the main known or can be prepared by customary methods.

The compounds of the general formula (IV) are new and can be prepared, for example, as described above.

The compounds of the general formula (I) according to the invention exhibit an unforeseeable, useful range of pharmacological action.

The compounds according to the invention have a specific A II-antagonistic action, since they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, disorders of the brain function, ischemic cerebral diseases, peripheral circulatory disorders, functional disorders of the kidney and adrenal gland, bronchospastic diseases and respiratory tract diseases having a vascular component, sodium retention and oedemas.

Investigation of the inhibition of the contraction induced by agonists

Rabbits of either sex are stunned by a blow to the back of the head and exsanguinated, or in some cases anaesthetized with Nembutal (about 60–80 mg/kg i.v.) and sacrificed by opening the thorax. The thoracic aorta is removed, freed from adhering connective tissue, divided into ring segments 1.5 mm wide and individually transferred under an initial loading of about 3.5 g to 10 ml organ baths containing Krebs-Henseleit nutrient solution, which is temperature-controlled at 37° C. and aerated with 95% $O_2$/ 5% $CO_2$, of the following composition: 119 mmol/l NaCl; 2.5 mmol/l $CaCl_2 \times 2H_2O$; 1.2 mmol/l $KH_2PO_4$; 10 mmol/l glucose; 4.8 mmol/l KCl; 1.4 mmol/l $MgSO_4 \times 7$ $H_2O$ and 25 mmol/l $NaHCO_3$.

The contractions are detected isometrically by Statham UC2 cells by means of bridge amplifiers (ifd Mülheim or DSM Aalen) and digitalized and assessed by means of A/D converters (System 570, Keithley Munich). Agonist dose response curves (DRC) are carried out hourly. With each DRC, 3 or 4 individual concentrations are applied to the baths at a 4 min interval. After the end of the DRC and subsequent washing-out cycles (16 times in each case about 5 sec/min with the abovementioned nutrient solution), a 28-minute rest or incubation phase follows, during which the contractions as a rule reach the starting value again.

The height of the 3rd DRC, in a normal case, is used as a reference variable for the assessment of the test substance to be investigated in further runs, which is applied to the baths in the following DRCs in increasing doses in each case at the start of the incubation period.

Each aorta ring is in this case stimulated for the whole day, always with the same agonist.

| Ex. No.: 9 | $IC_{50}$ [nM]: 61 | |
|---|---|---|
| Agonists and their standard concentrations (application volume per individual dose = 100 µl): | | |
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $3 \times 10^{-8}$; $3 \times 10^{-8}$; $3 \times 10^{-7}$ | g/ml |

For the calculation of the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarization or other agonists was not inhibited or only weakly inhibited at high concentrations.

Blood pressure measurements on the angiotensin II-infused rat

Male Wistar rats (Moellegaard, Copenhagen, Denmark) having a body weight of 300–350 g are anaesthetized with thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 µg/kg/min) is started. As soon as the blood pressure values have reached a stable plateau, the test substances are either administered intravenously or orally as a suspension or solution in 0.5% Tylose.

Determination of the antihypertensive activity in conscious hypertensive rats

The oral antihypertensive activity of the compounds according to the invention was tested in conscious rats using surgically induced unilateral renal artery stenosis. To do this, the right renal artery was constricted with a silver clip of 0.18 mm internal width. In this form of hypertension, the plasma renin activity is increased in the first six weeks after intervention.

The arterial blood pressure of these animals was measured non-invasively at defined time intervals after substance administration using the "tail cuff". The substances to be tested were suspended in a Tylose suspension and administered intragastrically ("orally") in various doses by stomach tube. The compounds according to the invention reduce the arterial blood pressure of the hypertensive rats at a clinically relevant dose.

Additionally, the compounds according to the invention inhibit the specific binding of radioactive angiotensin II in a concentration-dependent manner.

Interaction of the compounds according to the invention with the angiotensin II receptor in membrane fractions of the adrenal gland cortex (bovine)

Bovine adrenal gland cortices (AGC), which have been freshly removed and carefully freed from medulla from capsule, are comminuted in sucrose solution (0.32M) with the aid of an Ultra-Turrax (Janke & Kunkel, Staufen i.B.) to give a coarse membrane homogenate and are partially purified in two centrifugation steps to give membrane fractions. The receptor binding investigations are carried out on partially purified membrane fractions of bovine AGC using radioactive angiotensin II in an assay volume of 0.25 ml, which specifically contains the partially purified membranes (50–80 µg), $^3$H-angiotensin II (3–5 nM), test buffer solution (50 mM Tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The analysis of the raw data was carried out using computer programs to give $K_i$ or $IC_{50}$ values ($K_i$: $IC_{50}$ values corrected for the radioactivity used; $IC_{50}$ values: concentration at which the substance to be investigated causes a 50% inhibition of the specific binding of the radioligand).

TABLE A

| Ex. No. | $IC_{50}$ [nM] |
|---|---|
| 2 | 210 |
| 9 | 16 |

Investigation of the inhibition of the proliferation of smooth muscle cells by the compounds according to the invention To determine the antiproliferation action of the compounds, smooth muscle cells are used which are obtained from aortas of rats by the media explant technique [R. Ross, J. Cell. Biol. 50, 172, 1971]. The cells are inoculated in suitable culture dishes, as a rule 96-hole plates, and cultured in 5% $CO_2$ at 37° C. for 2–3 days in medium 199 containing 7.5% FCS and 7.5% NCS, 2 mM L-glutamine and 15 mM HEPES, pH 7.4. The cells are then synchronized by withdrawal of serum for 2–3 days and then stimulated into growth with serum or other factors. Test compounds are simultaneously added. After 16–20 hours, 1 µCi of $^3$H-thymidine is added and after a further 4 hours the incorporation of this substance into the TCA-precipitatable DNA of the cells is determined. To determine the IC$_{50}$ values, the active compound concentration is calculated which, on sequential dilution of the active compound, causes half-maximum inhibition of the thymidine incorporation produced by 10% FCS.

TABLE B

| Ex. No. | IC$_{50}$ [nM] |
|---|---|
| 14 | 120 |
| 23 | 43 |

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of about 0.001 to 1 mg/kg, preferably about 0.01 to 0.5 mg/kg, of body weight to achieve effective results, and in the case of oral administration the dose is about 0.01 to 20 mg/kg, preferably about 0.1 to 10 mg/kg, of body weight.

In spite of this, it may sometimes be necessary to deviate from the amounts mentioned, namely depending on the body weight or the type of application route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

Eluents
(A) Dichloromethane/methanol=20:1
(B) Dichloromethane/methanol=9:1
(C) Dichloromethane/methanol/glacial acetic acid=9:1:0.1
(D) Dichloromethane/methanol=95:5
(E) Petroleum ether/ethyl acetate=3:7
(F) Dichloromethane/methanol/ammonia=9:1:0.1
(G) Ethyl acetate
(H) Ethyl acetate/methanol=10:1
(I) Dichloromethane/methanol=10:1
(J) Petroleum ether/ethyl acetate=1:1

Starting compounds

EXAMPLE I

Methyl p-tolylacetate

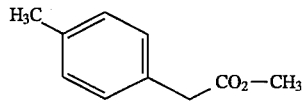

33 g (220 mmol) of p-tolylacetic acid are dissolved in 260 ml of 2,2-dimethoxypropane at room temperature, treated with 20 ml of conc. HCl and stirred for 2.5 h. For working up, the mixture is concentrated, the residue is taken up in methanol, the solution is concentrated again, the residue is redissolved in ethyl acetate, the solution is dried over sodium sulphate and filtered, and the solvent is removed.

Yield: 35.6 g (217 mmol) 99% of theory
$R_f$=0.23 (toluene/ethyl acetate=3:1)

EXAMPLE II

Methyl 2-isopropyl-2-p-tolylacetate

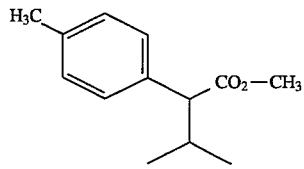

36.2 g (0.20 mol) of methyl p-tolylacetate are dissolved in 150 ml of DMF and the solution is added dropwise at 0° C. with stirring to a solution of 29.6 g (0.26 mol) of potassium tert-butoxide. After 30 minutes, 25 ml (0.26 mol) of 2-bromopropane, dissolved in 100 ml of DMF, are slowly added so that the temperature does not exceed 5° C. After stirring overnight, for working up, the mixture is concentrated, the residue is treated with ether and water, the mixture is shaken, the organic phase is separated off, the aqueous phase is extracted a further two times, and the combined organic phases are dried over sodium sulphate, filtered and concentrated.

Yield: 36.3 g (0.18 mol) 88% of theory
$R_f$=0.85 (toluene/ethyl acetate 9:1)

EXAMPLE III

Methyl 2-isopropyl-2-p-(bromomethyl) phenylacetate

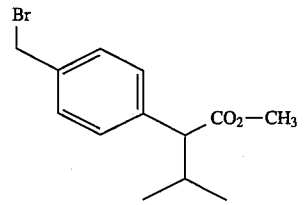

36.2 g (0.18 mol) of the compound from Example II are treated with 0.9 g (36 mmol) of N-bromosuccinimide and 1.5 g (10 mmol) of azabisisobutyronitrile under reflux with 100 ml of carbon tetrachloride. After the reaction has subsided, 0.9 g of N-bromosuccinimide is correspondingly added a further five times (total 0.21 mol). After reflux for 1 h, for working up, the mixture is cooled to 0° C., filtered concentrated and chromatographed on silica gel 60 (eluent: petroleum ether/ether=9:1).

15

Yield: 37.5 g (0.13 mol) 73% of theory
$R_f$=0.51 (petroleum ether/ether=9:1)
Preparation Examples

EXAMPLE 1

Methyl 2-[4-{2-cyclopropyl-5,7-dimethyl-imidazo-[4,5-b]pyridin-3-yl-methyl}phenyl]-2-isopropylacetate

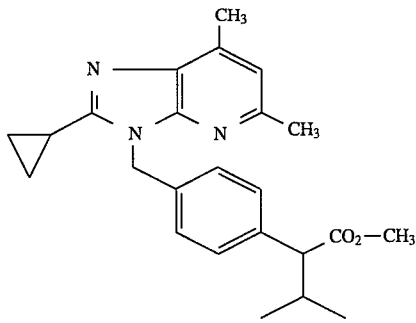

750 mg (4 mmol) of 2-cyclopropyl-5,7-dimethyl-imidazo[4,5-b]pyridine are dissolved in 4 ml of DMF and added at 0° C. with stirring to a suspension of 120 mg (80% strength, 4 mmol) of sodium hydride in 28 ml of DMF. After 15 minutes, a solution of 1.37 g (4.8 mmol) of the compound from Example III in 25 ml of DMF are added and the mixture is stirred at room temperature for a further 2 hours. For-working up, the mixture is added to ice-water, extracted twice with ethyl acetate, the combined organic phases are washed five times with saturated aqueous sodium chloride solution, dried over sodium Le A 29 515 sulphate, filtered and concentrated, and the residue is chromatographed on silica gel 60 (dichloromethane/methanol=100:5).
Yield: 1.03 g (2.6 mmol) 66% of theory
$R_f$=0.91 (dichloromethane/methanol=95:5)

EXAMPLE 2

Methyl 2-[4-{2-cyclopropyl-5,7-dimethyl-imidazo-[4,5-b]pyridin-3-yl-methyl}phenyl]-2-isopropylacetic acid

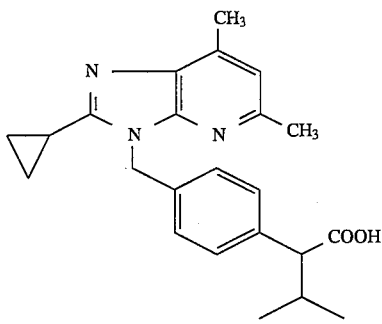

0.9 g (2.3 mmol) of the compound from Example I is treated with a solution of 0.19 g (4.6 mmol) of lithium hydroxide hydrate in 10 ml of water add 12 ml of dioxane at room temperature and the mixture is stirred overnight at room temperature. For working up, it is treated with ether and water and shaken, and the organic phase is separated and extracted a further two times with water. The combined organic phases are adjusted to pH 3 using 1N potassium hydrogen sulphate solution and extracted three times with ethyl acetate. The combined organic phases are dried over sodium sulphate, filtered and concentrated.
Yield: 0.84 g (2.2 mmol) 97% of theory
$R_f$=0.54 (dichloromethane/methanol=9:1)

16

EXAMPLE 3

2-[4-{2-cyclopropyl-5,7-dimethyl-imidazo-[4,5-b]pyridin-3-yl-methyl}phenyl]-2-isopropyl-N-(p-tolylsulphonyl)acetamide

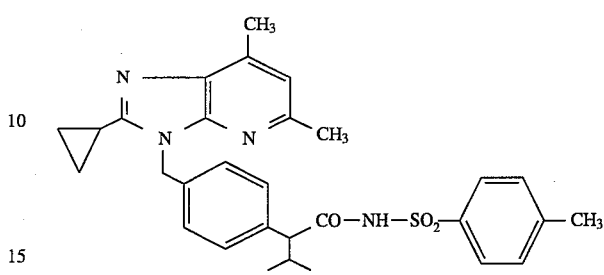

0.41 g (1.1 mmol) of the compound from Example 2 is dissolved in a mixture of 20 ml of dichloromethane and 2.5 ml of tetrahydrofuran under argon and cooled to 0° C. 0.3 ml (2.2 mmol) of triethylamine and 0.34 g (1.6 mmol) of dicyclohexylcarbodiimide are added and the mixture is stirred at –10° C. for 30 min. After addition of 0.22 g (1.3 mmol) of p-toluenesulphonamide, dissolved in 2 ml of dichloromethane, and 0.16 g (1.3 mmol) of N,N-4-dimethylaminopyridine, dissolved in 3 ml of dichloromethane, the mixture is allowed to come to room temperature overnight. For working up, it is treated with water, the mixture is shaken, insoluble matter is filtered off and the phases are separated. The aqueous phase is extracted a further two times with dichloromethane, and the combined organic phases are dried over sodium sulphate, filtered and concentrated, and the residue is chromatographed on silica gel 60 (petroleum ether/ethyl acetate=3:7, later pure ethyl acetate).
Yield: 0.26 g (0.49 mmol) 45% of theory

EXAMPLE 4 AND EXAMPLE 5

2-[4-{2-cyclopropyl-5,7-dimethyl-imidazo-[4,5-b]pyridin-3-yl-methyl}phenyl]-2-isopropylacetic acid (L-phenylglycinolamide

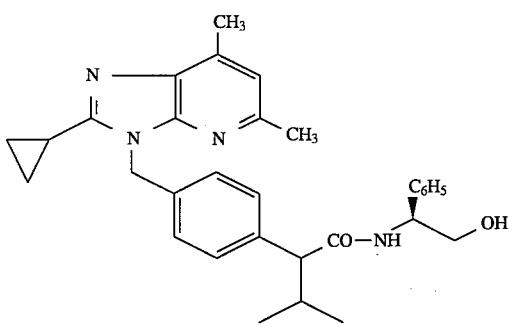

0.41 g (1.1 mmol) of the compound from Example 2 is dissolved in a mixture of 20 ml of dichloromethane and 2.5 ml of tetrahydrofuran under argon, treated with 0.25 g (1.6 mmol) of 1-hydroxy-1H-benzotriazole monohydrate and cooled to 0° C. 0.3 ml (2.2 mmol) of triethylamine and 0.34 g (1.6 mmol) of dicyclohexylcarbodiimide are added and the mixture is stirred at –10° C. for 30 min. After addition of 0.18 g (1.3 mmol) of L-phenylglycinol in 2.5 ml of dichloromethane, the mixture is allowed to come to room temperature overnight. For working up, it is treated with water, the mixture is shaken, insoluble matter is filtered off and the phases are separated. The aqueous phase is extracted a further time with dichloromethane, and the combined organic phases are dried over sodium sulphate, filtered and concentrated, and the residue is chromatographed on silica gel 60 (petroleum ether/ethyl acetate=7:3, later 3:7).

Yield: 0.4 g (0.8 mmol) 75% of theory. Diastereomers A and B

R$_f$=0.34 (ethyl acetate/petroleum ether=3:7) diastereomer A (Example 4)

R$_f$=0.25 (ethyl acetate/petroleum ether=3:7) diastereomer B (Example 5)

The compounds shown in Table 1 are prepared in analogy to the procedures of Examples 1–5:

TABLE 1

| Ex. No. | A | B | D | E | R² | R³ | * | R$_f$ [eluent] |
|---|---|---|---|---|---|---|---|---|
| 6 |  | CH₃ | CH₃ | N | H | OH | rac | 0.37 (B) |
| 7 |  | H | H | N | —CH(CH₃)₂ | OH | rac | 0.41 (C) |
| 8 |  | CH₃ | H | N | —CH(CH₃)₂ | OH | rac | 0.36 (D) |
| 9 |  | CH₃ | CH₃ | N | H | —NH—SO₂—C₆H₄—CH₃ | rac | 0.44 (E) |
| 10 |  | H | H | N | —CH(CH₃)₂ | —NH—SO₂—C₆H₄—CH₃ | rac | 0.39 (E) |
| 11 |  | CH₃ | H | N | —CH(CH₃)₂ | —NH—SO₂—C₆H₄—CH₃ | rac | 0.70 (B) |
| 12 |  | CH₃ | CH₃ | N | —CH(CH₃)₂ | —NH—SO₂—C₆H₄—CH₃ | rac | 0.62 (E) |
| 13 | n-C₄H₉ | H | H | CH | cyclopentyl | —NH—CH(C₆H₅)—CONH₂ | rac | 0.29 (A) |
| 14 | —C₆H₅ | H | H | N | cycloheptyl | —NH—CH(C₆H₅)—OH | rac | 0.50 (F) |

TABLE 1-continued

| Ex. No. | A | B | D | E | R² | R³ | * | R_f [eluent] |
|---|---|---|---|---|---|---|---|---|
| 15 | —C₆H₅ | CH₃ | H | N | cycloheptyl | —NH—CH(C₆H₅)—CH₂OH | ent A | 0.47 (G) |
| 16 | —C₆H₅ | CH₃ | H | N | cycloheptyl | —NH—CH(C₆H₅)—CH₂OH | ent B | 0.31 (G) |
| 17 | —C₆H₅ | H | H | N | cycloheptyl | —NH—CH(C₆H₄-p-Cl)—CH₂OH | ent A | 0.47 (B) |
| 18 | —C₆H₅ | H | H | N | cycloheptyl | —NH—CH(C₆H₄-p-Cl)—CH₂OH | ent B | 0.29 (B) |
| 19 | —C₆H₅ | CH₃ | H | N | cycloheptyl | —NH—CH(C₆H₄-p-Cl)—CH₂OH | ent A | 0.74 (H) |
| 20 | —C₆H₅ | CH₃ | H | N | cycloheptyl | —NH—CH(C₆H₄-p-Cl)—CONH₂ | ent B | 0.62 (H) |
| 21 | —C₆H₅ | H | H | N | cycloheptyl | —NH—CH(C₆H₅)—CONH₂ | ent A | 0.70 (H) |

TABLE 1-continued

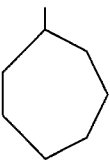

| Ex. No. | A | B | D | E | R² | R³ | * | R_f [eluent] |
|---|---|---|---|---|---|---|---|---|
| 22 | —C₆H₅ | H | H | N | cycloheptyl | —NH—CH(C₆H₅)—CONH₂ | ent B | 0.62 (H) |
| 23 | —C₆H₅ | CH₃ | H | N | cycloheptyl | —NH—CH(C₆H₅)—CONH₂ | rac | 0.42 (B) |
| 24 | —C₆H₅ | CH₃ | H | N | cycloheptyl | —NH—CH(C₆H₅)—CONH₂ | ent A | 0.80 (H) |
| 25 | —C₆H₅ | CH₃ | H | N | cycloheptyl | —NH—CH(C₆H₅)—CONH₂ | ent B | 0.61 (H) |
| 26 | —C₆H₅ | H | H | CH | cyclopentyl | OH | rac | 0.39 (I) |
| 27 | —C₆H₅ | H | H | CH | cyclopentyl | —HN—CH(C₆H₅)—CH₂OH | 2 dia | 0.68 (I) |
| 28 | —C₆H₅ | H | H | CH | cyclopentyl | —NH—CH(C₆H₅)—CONH₂ | 4 dia | 0.63 (I) |
| 29 | —C₆H₅ | H | H | CH | cyclopentyl | —OC(CH₃)₃ | rac | 0.27 (J) |

We claim:
1. A substituted imidazo[4,5-b]pyridine of the formula:

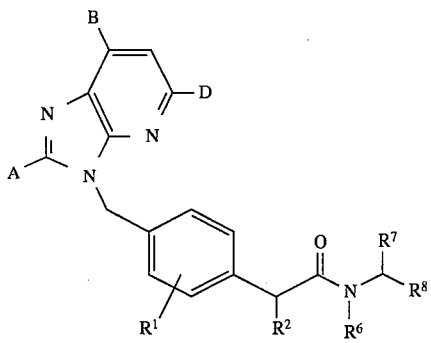

in which

A represents straight-chain or branched alkyl or alkenyl in each case having up to 8 carbon atoms; or
represents cycloalkyl having 3 to 8 carbon atoms; or
represents phenyl which is optionally substituted by halogen, nitro, hydroxyl, trifluoromethyl, trifluoromethoxy, straight-chain or branched alkyl, alkoxy or alkoxycarbonyl in each case having up to 6 carbon atoms, cyano or carboxyl;

B and D are identical or different and represent hydrogen, halogen or straight-chain or branched alkyl having up to 8 carbon atoms;

$R^1$ represents hydrogen, halogen, nitro, hydroxyl, trifluoromethyl, trifluoromethoxy, straight-chain or branched alkyl, alkoxy or alkoxycarbonyl in each case having up to 6 carbon atoms, cyano or carboxyl;

$R^2$ represents hydrogen, cycloalkyl having 3 to 8 carbon atoms or straight-chain or branched alkyl having up to 8 carbon atoms, which is optionally substituted by phenyl, carboxyl, hydroxyl, halogen, cyano, cycloalkyl having 3 to 8 carbon atoms or by straight-chain or branched alkoxy or alkoxycarbonyl in each case having up to 6 carbon atoms;

$R^6$ represents hydrogen, straight-chain or branched alkyl having up to 6 carbon atoms or phenyl;

$R^7$ represents phenyl which is optionally substituted up to 2 times by identical or different substituents selected from the group consisting of halogen, nitro, hydroxyl, trifluoromethyl, trifluoromethoxy, straight-chain or branched alkyl, alkoxy or alkoxycarbonyl in each case having up to 6 carbon atoms, cyano, carboxyl, cycloalkyl having 3 to 8 carbon atoms and phenyl; and $R^8$ represents carboxyl or straight-chain or branched alkoxycarbonyl having up to 6 carbon atoms; or
represents a group of the formula $-CH_2-OR^{11}$, $-CO-NR^{12}R^{13}$ or $-CH_2NR^{12}R^{13}$,
in which
$R^{11}$ represents hydrogen, phenyl or straight-chain or branched alkyl having up to 6 carbon atoms; and
$R^{12}$ and $R^{13}$ are identical or different and represent hydrogen, straight-chain or branched alkyl having up to 6 carbon atoms or phenyl; or $-SO_2-R^{10}$,
in which
$R^{10}$ represents straight-chain or branched alkyl having up to 6 carbon atoms, which is optionally substituted by phenyl, or represents phenyl, which is optionally substituted by straight-chain or branched alkyl having up to 4 carbon atoms;

an optical isomer thereof, where appropriate, or a salt thereof.

2. Substituted imidazo[4,5-b]pyridines and benzimidazoles according to claim 1, in which A represents straight-chain or branched alkyl or alkenyl in each case having up to 6 carbon atoms, or
represents cyclopropyl, cyclobutyl, cyclopentyl, cyclohexyl or cycloheptyl or represents phenyl which is optionally substituted by fluorine, chlorine, bromine, trifluoromethyl, carboxyl or straight-chain or branched alkyl, alkoxy or alkoxycarbonyl in each case having up to 4 carbon atoms, B and D are identical or different and represent hydrogen or straight-chain branched alkyl having up to 6 carbon atoms, E represents a nitrogen atom or the $-CH-$ group, $R^1$ represents hydrogen, fluorine, chlorine, bromine, trifluoromethyl, carboxyl or straight-chain or branched alkyl, alkoxy or alkoxycarbonyl in each case having up to 4 carbon atoms, $R^2$ represents hydrogen, cyclopropyl, cyclopentyl, cyclohexyl or cycloheptyl or represents straight-chain or branched alkyl having up to 6 carbon atoms, which is optionally substituted by phenyl, fluorine, chlorine, bromine, cyclopentyl, cyclohexyl or by straight-chain or branched alkoxy or alkoxycarbonyl in each case having up to 4 carbon atoms, $R^6$ denotes hydrogen or straight-chain or branched alkyl having up to 4 carbon atoms, $R^7$ denotes phenyl which is optionally substituted up to 2 times by identical or different substituents from the series consisting of fluorine, chlorine, bromine, trifluoromethyl, carboxyl, straight-chain or branched alkyl, alkoxy or alkoxycarbonyl in each case having up to 4 carbon atoms, cyclopentyl, cyclohexyl or phenyl, $R^8$ denotes carboxyl or straight-chain or branched alkoxycarbonyl having up to 4 carbon atoms, or denotes a group of the formula $-CH_2-OR^{11}$, $-CO-NR^{12}R^{13}$ or $-CH_2NR^{12}R^{13}$,
in which
$R^{11}$ denotes hydrogen or phenyl, or straight-chain or branched alkyl having up to 4 carbon atoms
and
$R^{12}$ and $R^{13}$ are identical or different and denote hydrogen or straight-chain or branched alkyl having up to 4 carbon atoms, appropriate in an isomeric form, and their salts.

3. Substituted imidazo[4,5-b]pyridines and benzimidazoles according to claim 1, in which A represents straight-chain or branched alkyl or alkenyl in each case having up to 4 carbon atoms, or
represents cyclopropyl, cyclopentyl, cyclohexyl or cycloheptyl, or represents phenyl, B and D are identical or different and represent hydrogen, methyl or ethyl, E represents a nitrogen atom or the $-CH-$ group, $R^1$ represents hydrogen, fluorine, chlorine, bromine, trifluoromethyl, trifluoromethoxy or methyl, $R^2$ represents hydrogen, cyclopropyl, cyclopentyl, cyclohexyl, cycloheptyl, benzyl or straight-chain or branched alkyl, which is optionally substituted by cyclopentyl or cyclohexyl, $R^6$ denotes hydrogen or methyl denotes phenyl which is optionally substituted by fluorine, chlorine, bromine, trifluoromethyl, trifluoromethoxy or methyl, $R^8$ denotes carboxyl or straight-chain or branched alkoxycarbonyl having up to 3 carbon atoms, or denotes a group of the formula —$CH_2O$—$R^{11}$, —CO—$NR^{12}R^{13}$ or —$CH_2NR^{12}R^{13}$ in which $R^{11}$ denotes hydrogen or straight-chain or branched alkyl having up to 3 carbon atoms and $R^{12}$ and $R^{13}$ are identical or different and denote hydrogen or methyl, if appropriate in an isomeric form, and their salts.

4. Substituted imidazo[4,5-b]pyridines and benzimidazoles according to claim 1, in which A represents straight-chain or branched alkyl having up to 4 carbon atoms, or represents cyclopropyl or cyclopentyl, or represents phenyl, B and D are identical or different and represent hydrogen or methyl, E represents a nitrogen atom or the CH group, $R^1$ represents hydrogen, fluorine or chlorine, $R^2$ represents hydrogen, cyclopentyl, cyclohexyl or cycloheptyl, or represents straight-chain or branched alkyl having up to 4 carbon atoms, and $R^6$ denotes hydrogen or methyl $R^7$ denotes phenyl which can optionally be substituted by fluorine, chlorine or methyl, denotes the group —$CH_2$—OH or —$CONH_2$, if appropriate in an isomeric form, and their salts.

5. A compound according to claim 1 wherein such compound is 2-[4-{2-cyclopropyl-5,7-dimethyl-imidazo-[4,5-b]pyridin-3-yl-methyl}phenyl]-2-isopropylacetic acid (L-phenylglycinolamide) of the formula

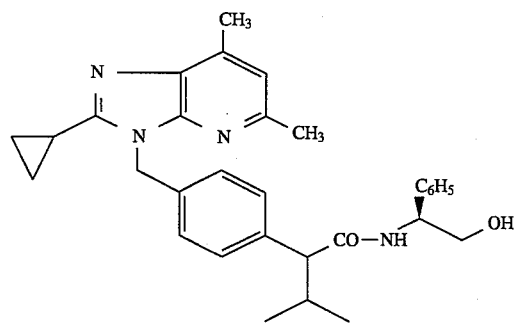

or a salt thereof.

6. A composition for the treatment of hypertension and atherosclerosis comprising an amount effective therefor of a compound or a salt thereof according to claim 1 and a pharmacologically acceptable diluent.

7. The method of treating hypertension and atherosclerosis in a patient in need thereof which comprises administering to such patient an amount effective therefor of a compound or a salt thereof according to claim 1.

* * * * *

UNITED STATES PATENT AND TRADEMARK OFFICE
CERTIFICATE OF CORRECTION

PATENT NO. : 5,527,809
DATED : June 18, 1996
INVENTOR(S) : Muller-Gliemann, et al.

It is certified that error appears in the above-indentified patent and that said Letters Patent is hereby corrected as shown below:

Col. 24, line 50    Before " appropriate " insert -- if --

Col. 25, line 1    Before " denotes " insert -- $R^7$ --

Col. 26, line 3    Before " denotes " insert -- $R^8$ --

Signed and Sealed this

Twelfth Day of November, 1996

Attest:

BRUCE LEHMAN

Attesting Officer    Commissioner of Patents and Trademarks